United States Patent [19]

Vishnupad et al.

[11] Patent Number: 4,950,475

[45] Date of Patent: Aug. 21, 1990

[54] NOVEL FILM-FORMING GELS WITH HIGH CONCENTRATIONS OF HUMECTANTS AND EMOLLIENTS

[75] Inventors: Mohan Vishnupad, Monroe; Jose Ramirez, Trumball, both of Conn.

[73] Assignee: Imaginative Research Associates, Inc., Bridgeport, Conn.

[21] Appl. No.: 221,292

[22] Filed: Jul. 19, 1988

[51] Int. Cl.$^5$ .................... A61K 31/745; A61K 31/21
[52] U.S. Cl. .......................................... 424/83; 514/23; 514/506; 514/588; 514/944; 514/953
[58] Field of Search .................. 424/83; 514/944, 953, 514/506, 588, 23; 524/202, 603

[56] References Cited

U.S. PATENT DOCUMENTS

| | | | |
|---|---|---|---|
| 3,536,816 | 10/1970 | Kellner | 514/786 |
| 3,666,690 | 5/1972 | Bann | 252/547 |
| 3,734,874 | 5/1973 | Kibler et al. | 524/603 |
| 3,949,742 | 4/1976 | Nowakowski | 128/155 |
| 4,017,641 | 4/1977 | DiGiulio | 514/786 |
| 4,059,458 | 11/1977 | Germino et al. | 106/213 |
| 4,128,507 | 12/1978 | Mitzner | 252/522 |
| 4,233,196 | 11/1980 | Sublett | 524/202 |
| 4,300,580 | 11/1981 | O'Neill et al. | 132/7 |
| 4,304,900 | 12/1981 | O'Neill | 528/290 |
| 4,304,901 | 12/1981 | O'Neill et al. | 528/290 |
| 4,335,220 | 3/1982 | Coney | 523/414 |
| 4,379,755 | 4/1983 | Yamada et al. | 252/312 |
| 4,393,048 | 7/1983 | Mason, Jr. et al. | 424/619 |
| 4,502,976 | 3/1985 | Heller | 252/315.4 |
| 4,690,774 | 9/1987 | Vishnupad et al. | 252/309 |

OTHER PUBLICATIONS

"Eastman AQ Polymer—A Unique Dispersant for Hydrophobic Materials", by M. J. Idacavage.

*Primary Examiner*—John W. Rollins
*Attorney, Agent, or Firm*—Morgan & Finnegan

[57] ABSTRACT

Novel film-forming gel compositions are described comprising from 10–40% by weight of a water dissipatable polymer, from 10 to 40% by weight of humectants and 20–60% by weight of water. The gel compositions may also be in the form of an emulsion comprising from 15–30% by weight of a water dissipatable polymer, from 15 to 35% by weight of humectants, up to 40% by weight of emollients, from 15 to 35% by weight water and a small amount of emulsifier. Additionally the gels of the present invention may contain optional agents such as, for example, coloring agents, pigments, preservatives, medical agents, cosmetic agents or agents to modify the refractive index of the gel.

6 Claims, No Drawings

NOVEL FILM-FORMING GELS WITH HIGH CONCENTRATIONS OF HUMECTANTS AND EMOLLIENTS

FIELD OF THE INVENTION

This invention relates generally to film-forming gels. More specifically, this invention relates to film-forming gels having high concentrations of humectants and/or emollients. These novel film-forming gels may be in the form of an emulsion.

BACKGROUND OF THE INVENTION

Many compositions used for skin treatments contain emollients or humectants such as petroleum jelly. Such compositions are used for many dermatological applications such as moisturizing, amelioration of wrinkles, prevention of chaffing, or wound healing. When applied to the skin, these compositions tend to be greasy, and therefore tend to transfer onto and stain clothing or other surfaces which contact the area of application.

Water soluble gels that form protective films of various types are known. For example, U.S. Pat. No. 4,393,048 discloses a water soluble hydrogel of alkali metal alginate and glycerine that dries to a non-toxic, pliable protective film. U.S. Pat. No. 3,489,690 describes water-and-oil emulsions which can contain waxy film formers like petroleum jelly to form films which are nonpliable, tacky and transferable when rubbed between surfaces. U.S. Pat. No. 3,949,742 discloses a transparent medical dressing which performs as a synthetic film over skin wounds comprised of a laminate of a thin layer of non-porous segmented polyurethane secured to foam. U.S. Pat. No. 3,734,874 describes water-dissipatable, meltable polyesters that are useful as adhesives, coating materials, films, packaging materials and other products that can be dissolved, dispersed or otherwise dissipated in water or acqueous solutions. Although the polymers described in U.S. Pat. No. 3,734,874 may not pose the problem of transferring to surfaces in contact with the area of application, they do not contain humectants or emollients to serve as satisfactory skin treatment compositions.

OBJECTS OF THE INVENTION

It is therefore an object of the present invention to provide novel film-forming gels with high humectant and/or emollient content.

A further object of the present invention is to provide novel gels with humectant or emollient content of up to 40% by weight based on the total composition of the gel and which, upon application to a surface, dry to form films to prevent the transfer of any portion of the composition to other surfaces.

A further object of this invention is to provide gels which can carry pigments and colorants and which upon application to a surface, dry to form films to prevent the transfer of the composition to other surfaces.

A further object of this invention is to provide gels which form a water soluble film.

A further object of this invention is to provide gels which form a film and can carry topical treatments and which when exposed to a high water content environment, will release said treatments.

Another object of this invention is to provide a film which can be applied to a surface to protect, moisturize and/or treat the surface.

Another object of this invention is to provide compositions containing sunscreens which can be applied as a gel or a pre-formed article (tape, pad, etc.) to a surface to protect the surface from sunlight damage.

Another object of this invention is to provide films which can be applied to wounds, cuts and burns as dressings, bandages and patches, in the form of a tape or other precut forms.

It is also an object of this invention to provide gels which can be cast or molded into articles of various shapes and sizes.

Another object of this invention is to provide gels which form thick films and casts which may be used or prosthetic implants, inserts and for transdermal drug delivery patches.

Another object of this invention is to provide compositions containing fragrances, insect repellents and similar chemical compositions which are used in gel form or as a pre-formed article.

These and other advantages of the present invention will be apparent to those skilled in the art from the following description of the invention.

SUMMARY OF THE INVENTION

It has now been found that the objectives of this invention may be realized by forming a gel composition comprising from 10–40% by weight of a water dissipatable polymer, from 10% to 40% by weight of humectants and 20–60% by weight of water. The gel compositions may also be in the form of an emulsion comprising from 15–30% by weight of a water dissipatable polymer, from 15 to 35% by weight of humectants, up to 40% by weight of emollients, from 15 to 35% by weight water and a small amount of emulsifier. Additionally, the gels of the present invention may contain optional agents such as, for example, coloring agents, pigments, preservatives, medical agents, and cosmetic agents.

DETAILED DESCRIPTION OF THE INVENTION

The novel gels of the present invention comprise: (a) a water dissipatable polymer in an amount from 10 to 40% by weight based on the total weight of the composition; (b) a humectant in an amount from 10 to 40% by weight based on the total weight of the composition; and (c) water in an amount from 20 to 60% by weight based on the total weight of the composition.

The novel gels of the present invention may also be in the form of an emulsion. The emulsion-type gels of the present invention comprise: (a) a water dissipatable polymer in an amount from 15% to 30% by weight based on the total weight of the composition; (b) a humectant in an amount from 15% to 35% by weight based on the total composition; (c) an emollient in an amount up to 40% by weight based on the total composition; (d) water in an amount from 15% to 35% by weight based on the total composition; and (e) an emulsifier in an amount from 0.01% to 5% based on the total weight of the composition.

Polymers useful in the present invention must be capable of plasticizing with the humectant component of the composition to form a water soluble film. Polymers suitable for use in this invention include the water-dissipatable polyesters and polyesteramides described in U.S. Pat. No. 3,734,874 to Kibler, et al., U.S. Pat. No. 4,233,196 to Sublett and U.S. Pat. No. 4,304,901 to O'-Neill, et al. A preferred water dissipatable polyester is commercially available as Eastman AQ 55S polymer.

Examples of humectants useful in this invention include glycerine, sorbitol, polyethylene glycol, propylene glycol, polysaccharides (such as fructose, glucose, maltose, etc.), corn syrup, polyols, urea and derivatives and natural honey. Preferred humectants are propylene glycol and glycerine.

In forming the emulsion-type gels of the present any emollient may be used. Emollients useful in this invention include hydrocarbon oils and semi-solid hydrocarbons, lanolin and derivatives, and esters commonly used in the cosmetic field.

Any suitable emulsifier to obtain a stable film forming emulsion may be used. The choice of appropriate emulsifier for use in this invention will depend upon the compositions of the other components selected. The selection of an appropriate emulsifier for a given system is within the purview of one skilled in the art.

Optionally, a wide variety of agents may be incorporated into the compositions of this invention for a variety of purposes. For example, coloring agents, pigments, perfumes or preservatives may be added to create a product having characteristics desirable in a consumer product. Medical agents may also be incorporated to prevent infection, kill microorganisms, promote healing or sooth itching. Cosmetic agents may also be incorporated to moisturize, reduce wrinkles, act as a deodorant or cover moles or blemishes.

The gels of this invention may be applied directly to the skin and may have the same general feel and appearance as conventional gels, jellies or emulsions. When allowed to dry, however, the films formed by the gels of this invention provide protection to the skin and render the humectant component, emollient component or any optional agents in the composition non-transferrable. Furthermore, the humectant, emollient or optional agents are in occlusive contact with the surface and contact the area of application to protect, moisturize, heal, etc. Since the films formed by the gels of this invention are water soluble, they can be washed off when desired.

The gels of this invention may also contain fragrances, insect repellants and like chemicals. When allowed to dry, the films formed by the gels of this invention provide the benefits inherent in such compounds by the slow release of the fragrances, insect repellants, etc. when the film is exposed to water in the immediate environment, i.e. humidity in the air or water from a natural or artificial source.

The gels of this invention may also be pre-formed into any shape. For example, the gels of this invention may be applied to a surface or poured into a tray and dried to a film which may be cut into a tape or a pad of any shape. Methods for forming tapes or pads from the gels of this invention also include extruding the gel in a partially dried state and allowing it to dry to a desirable thickness. The tape or pad so formed from the gels of this invention can then be applied or secured to the skin or a surface to be treated, protected or lubricated. These pre-formed tapes or pads may be applied to wounds, cuts and burns as dressing, bandages and patches. The novel gels may also be cast or molded into any shape or form. When so cast the pre-formed articles may be useful as prosthetic implants, inserts for transdermal drug delivery patches.

The following examples illustrate how the film-forming gels of this invention may be formed.

EXAMPLE I

A film-forming gel was produced having the following composition:

|  | % By Wt. |
| --- | --- |
| Eastman AQ 55S Polymer | 30.00 |
| Propylene Glycol | 40.00 |
| Water | 30.00 |

The film-forming gel of EXAMPLE I was prepared by placing the appropriate amounts of propylene glycol and water into a suitable container and heating the mixture to 80° C. The heated aqueous phase thus produced was transferred to a blender and the appropriate amount of polymer was gradually added with the blender providing high shear mixing to dissolve the solids. When all the solids were added, high shear mixing was continued until a clear, straw colored, thick gel was produced. The gel was then cooled to room temperature.

EXAMPLE II

An emulsion-type film-forming gel of this invention was prepared having the following composition:

|  | % By Wt. |
| --- | --- |
| Eastman AQ 55S polymer | 24.0 |
| Propylene Glycol | 32.0 |
| Petroleum Jelly | 19.5 |
| Polyglycerol Isostearate | 0.5 |
| Water | 24.0 |

The film-forming gel of EXAMPLE II was formed by placing appropriate amounts of water and propylene glycol in a suitable container and heating the mixture to 80° C. The heated aqueous phase thus produced was transferred to a blender and the appropriate amount of polymer was gradually added with the blender providing high shear mixing to dissolve the solids. When all the solids were added, high shear mixing was continued until a clear, straw colored, thick gel was produced. The petroleum jelly was then melted at 70° C. and the emulsifier (polyglycerol isostearate) was added thereto to form the oil phase. The aqueous phase gel was transferred to a beaker, the oil phase was added at 70° C. and the aqueous and oil phases were homogenized using an Epinbach homomixer until a smooth emulsion was produced. The emulsion was then cooled to room temperature.

EXAMPLES III–XVII

The following are additional specific examples of film-forming gels of this invention.

EXAMPLE III

|  | % By Wt. |
| --- | --- |
| EXAMPLE III | |
| Eastman AQ 55S polymer | 29.80 |
| Propylene Glycol | 39.75 |
| Irgasan | 0.15 |
| Fragrance | 0.50 |
| Water | 29.80 |
|  | 100.00% |
| EXAMPLE IV | |
| Eastman AQ 55S polymer | 24.00 |
| Propylene Glycol | 32.00 |

-continued

| | % By Wt. |
|---|---|
| Irgasan | 0.15 |
| Petroleum Jelly | 19.35 |
| Polyglycerol Isostearate | 0.50 |
| Water | 24.00 |
| | 100.00% |

EXAMPLE V

| | |
|---|---|
| Eastman AQ 55S polymer | 27.00 |
| Propylene Glycol | 36.00 |
| Menthol | 10.00 |
| Water | 27.00 |
| | 100.00% |

EXAMPLE VI

| | |
|---|---|
| Eastman AQ 55S polymer | 24.00 |
| Propylene Glycol | 32.00 |
| Menthol | 9.50 |
| Petroleum Jelly | 10.00 |
| Polyglycerol Isostearate | 0.50 |
| Water | 24.00 |
| | 100.00% |

EXAMPLE VII

| | |
|---|---|
| Eastman AQ 55S polymer | 24.00 |
| Propylene Glycol | 32.00 |
| Methyl Salicylate | 10.00 |
| Petroleum Jelly | 9.50 |
| Polyglycerol Isostearate | 0.50 |
| Water | 24.00 |
| | 100.00% |

EXAMPLE VIII

| | |
|---|---|
| Eastman AQ 55S polymer | 20.85 |
| Propylene Glycol | 27.80 |
| Methyl Salicylate | 10.00 |
| Polyglycerol Isostearate | 0.50 |
| Cyclomethicone (and) Dimethicone Copolyol | 20.00 |
| Water | 20.85 |
| | 100.00% |

EXAMPLE IX

| | |
|---|---|
| Eastman AQ 55S polymer | 25.00 |
| Glycerin | 30.00 |
| Polyglycerol Isostearate | 0.50 |
| Petroleum jelly | 20.00 |
| Water | 24.50 |
| | 100.00% |

EXAMPLE X

| | |
|---|---|
| Eastman AQ 55S polymer | 22.00 |
| Glycerin | 15.00 |
| Propylene glycol | 15.00 |
| Polyglycenol Isostearate | 0.50 |
| Petroleum jelly | 20.00 |
| Water | 27.50 |
| | 100.00% |

EXAMPLE XI

| | |
|---|---|
| Eastman AQ 55S polymer | 20.00 |
| Glycerin | 24.00 |
| Polyglycerol Isostearate | 0.50 |
| Petroleum Jelly | 16.00 |
| Minoxidil | 0.10 |
| Fragrance | 0.40 |
| Water | 39.00 |
| | 100.00% |

EXAMPLE XII

| | |
|---|---|
| Eastman AQ 55S polymer | 22.00 |
| Petroleum Jelly | 49.00 |
| Glycerin | 29.00 |
| | 100.00% |

EXAMPLE XIII

| | |
|---|---|
| Eastman AQ 55S polymer | 36.46 |
| Glycerin | 48.56 |
| Escalol 507 | 13.64 |
| Polyglycerol Isostearate | 1.34 |
| | 100.00% |

EXAMPLE XIV

| | |
|---|---|
| Eastman AQ 55S polymer | 25.00 |
| Glycerin | 30.00 |
| Polyglycerol Isostearate | 0.50 |
| Alpha Hydroxy Acids | 1.00 |

-continued

| | % By Wt. |
|---|---|
| Petroleum jelly | 20.00 |
| Water | 23.50 |
| | 100.00% |

EXAMPLE XV

| | |
|---|---|
| Eastman AQ 55S polymer | 25.00 |
| Glycerin | 30.00 |
| Polyglycenol Isostearate | 0.50 |
| Cis, Trans. Retinoic Acids | 0.01 |
| Petroleum jelly | 20.00 |
| Water | 24.49 |
| | 100.00% |

The film-forming gels of this invention were tested for transferability. The gels of EXAMPLES I and II above, were compared to conventional oil-in-water emulsions and creams. The convention oil-in-water products employed were a hand lotion comprising an oil-in-water emulsion, a cleansing Cold Cream and Petroleum Jelly U.S.P., all of which are commercially available. To test transferability, a 0.5 gram sample of each product was spread on the forearm and allowed to dry for 2 minutes and 5 minutes. A dry, pre-weighed facial tissue was then pressed on the area of application. The tissue was re-weighed after the pressing contact with the product and the percentage of product transferred was calculated. The results of these tests are reported in Table A.

TABLE A

| Product | Drying Time | % of Product Transferred |
|---|---|---|
| Hand Lotion | 2 min | 42% |
| (Oil-in-Water Emulsion) | 5 min | 34% |
| Petroleum Jelly U.S.P. | 2 min | 56% |
| | 5 min | 52% |
| Cleansing Cold Cream | 2 min | 62% |
| | 5 min | 68% |
| EXAMPLE I | 2 min | 12% |
| | 5 min | 0% |
| EXAMPLE II | 2 min | 22% |
| | 5 min | 0% |

The results in TABLE A show that the gels of this invention are significantly less transferrable compared to conventional oil-in-water emulsions and creams after 2 minutes of drying and become non-transferrable within 5 minutes.

Although particular illustrative embodiments of the present invention have been described herein, the present invention is not limited to these particular embodiments. Various changes and modifications may be made thereto by those skilled in the art without departing from the spirit or scope of the invention, which is defined by the appended claims.

We claim:
1. A film-forming gel comprising:
   (a) equal parts of a water-dissipatable polyester and water in a combined amount from 30% to 80% by weight of the total composition: and
   (b) humectant in an amount from 10% to 40% by weight of the total composition;
   said gel composition forming a non-transferrable film upon drying.
2. A film-forming gel comprising:
   (a) equal parts of a water-dissipatable polyesteramide and water in a combined amount from 30% to 80% by weight of the total composition; and

(b) humectant in an amount from 10% to 40% by weight of the total composition;
said gel composition forming a non-transferrable film upon drying.

3. A film-forming gel according to claim 1 or 2 wherein the humectant is selected from the group consisting of glycerine, sorbitol, polyethylene glycol, propylene glycol, fructose, glucose, maltose, corn syrup, urea and natural honey.

4. A film-forming gel comprising:
(a) water-dissipatable polyester in an amount from 15% to 30% by weight on the total composition;
(b) humectant in an amount from 15% to 35% by weight based on the total composition;
(c) emollients up to 40% by weight based on the total composition;
(d) water in an amount from 18% to 24% by weight based on the total composition; and
(e) emulsifier in an amount from 0.01% to 5% by weight based on the total composition;
said gel composition forming a non-transferrable film upon drying.

5. A film-forming gel comprising:
(a) water-dissipatable polyesteramide in an amount from 15% to 30% by weight based on the total composition;
(b) humectant in an amount from 15% to 35% by weight based on the total composition;
(c) emollients up to 40% by weight based on the total composition;
(d) water in an amount from 18% to 24% by weight based on the total composition; and
(e) emulsifier in an amount from 0.01% to 5% by weight based on the total composition;
said gel composition forming a non-transferrable film upon drying.

6. A film-forming gel according to claim 4 or 5 wherein the humectant in selected from the group consisting of glycerine, sorbitol, polyethylene glycol, propylene glycol, fructose, glucose, maltose, corn syrup, urea and natural honey.

* * * * *